United States Patent
Li et al.

(10) Patent No.: US 7,126,009 B2
(45) Date of Patent: Oct. 24, 2006

(54) PALLADIUM CATALYZED INDOLIZATION OF 2-BROMO OR CHLOROANILINES

(75) Inventors: Guisheng Li, Richmond, VA (US); Jianxiu Liu, Richmond, VA (US); Zhi-Hui Lu, Glen Allen, VA (US); Frank Roschangar, Glen Allen, VA (US); Chris Hugh Senanayake, Brookfield, CT (US); Ming Shen, Waltham, MA (US)

(73) Assignee: Boehringer Ingelheim International, GmbH, Ingelheim (DE)

( * ) Notice: Subject to any disclaimer, the term of this patent is extended or adjusted under 35 U.S.C. 154(b) by 67 days.

(21) Appl. No.: 11/079,636

(22) Filed: Mar. 14, 2005

(65) Prior Publication Data
US 2005/0209465 A1    Sep. 22, 2005

Related U.S. Application Data

(60) Provisional application No. 60/553,596, filed on Mar. 16, 2004.

(51) Int. Cl.
C07D 209/04 (2006.01)
C07D 209/08 (2006.01)
C07D 209/12 (2006.01)
C07D 209/24 (2006.01)
C07F 7/10 (2006.01)

(52) U.S. Cl. .................... 548/508; 548/406; 548/407; 548/503; 546/277.4; 546/15

(58) Field of Classification Search ................ 548/508
See application file for complete search history.

(56) References Cited

OTHER PUBLICATIONS

R.C. Larock, et al. "Synthesis of 2,3-Disubstituted Indoles via Palladium-Catalyzed Annulation of Internal Alkynes", Journal of Organic Chemistry, 1998, vol. 63, pp. 7652-7662 XP 002375382.
F. Maassarani, et al. "Controlled Synthesis of Heterocyclic Compounds through Ring Enlargement by Alkyne Insertions into the PD-C Bonds of Cyclopalladated Amines Followed by Subsequent Ring Closure", Organometallics, 1987, vol. 6, pp. 2029-2043 XP-002375383.
F. Maassarani, et al. "Stepwise Insertion of One, Two, and Three Alkyne Molecules into the Pd-C Bond of a Six-Membered Palladocycle. One-Pot Synthesis of Spirocyclic Compounds", Organometallics, 1987, vol. 6, pp. 2043-2053 XP-002375384.
F. Maassarani, et al., "Selective hetero- and carbo-cycle synthesis via masked cyclopalladated secondary amine and ketone functions", J. Organometallic Chemistry, vol. 466, 1994, pp. 265-271 XP-002375385.
Database Zregistry [Online] Dec. 12, 1987, XP002377297 retrieved from STN RN: 111783-46-1 ABSTRACT.
Database Zregistry [Online] Nov. 16, 1984, XP002377298, retrieved from STN RN: 2486-71-7 ABSTRACT.
Database Zregistry [Online] Nov. 16, 1984, XP002377299, retrieved from STN RN: 95-74-9 ABSTRACT.
M. Shen, et al. "The First Regioselective Palladium-Catalyzed Indolization of 2-Bromo- or 2-Chloroanillnes with Internal Alkynes: A New Approach to 2,3-Disubstituted Indoles", Organic Letters, vol. 6, No. 22, pp. 4129-4132 XP-002375386.

*Primary Examiner*—Kamal A. Saeed
*Assistant Examiner*—Jason M. Nolan
(74) *Attorney, Agent, or Firm*—Michael P. Morris; Mary-Ellen M. Devlin; David Dow

(57) ABSTRACT

The present invention provides a method for making substituted indole compounds of general formula III comprising the step of:
(a) reacting a 2-bromoaniline or 2-chloroaniline of general formula (I)

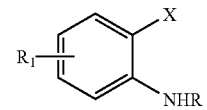

(I)
wherein: X, R and $R_1$ are defined herein
with a substituted acetylene of formula (II)

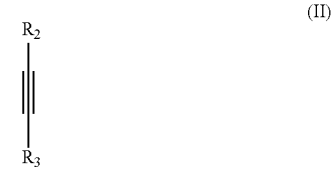

(II)

wherein $R_2$ and $R_3$ are defined herein in the presence of a palladium catalyst, a ligand, and a base in a solvent at a suitable temperature to give a compound of formula (III);

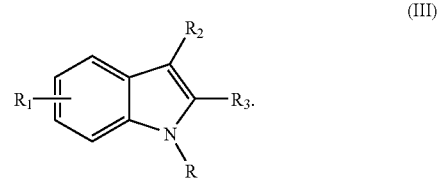

(III)

10 Claims, No Drawings

PALLADIUM CATALYZED INDOLIZATION OF 2-BROMO OR CHLOROANILINES

RELATED APPLICATIONS

This application claims benefit of U.S. provisional application Ser. No. 60/553,596, filed on Mar. 16, 2004 and its contents are incorporated herein.

FIELD OF THE INVENTION

The invention relates to the field of pharmaceuticals and more specifically to processes for making substituted indole compounds.

BACKGROUND OF THE INVENTION

The indole nucleus is a prominent structure motif found in numerous natural products and pharmaceutically active compounds. Examples of substituted indoles used in the preparation of pharmaceutical agents and as pharmaceutical agents themselves include Indomethacin, an anti-inflammatory medicine, Tropesin, an anti-inflammatory and analgesic agent, Mebhydroline, antihistaminic agent and Vinpocetine, a vasodilator agent. Other examples of indole compounds used as pharmaceutical agents those disclosed in U.S. patent application Ser. No. 10/198,384 and and U.S. provisional application 60/546,213, filed Feb. 20, 2004 the contents of which are incorporated herein by reference.

Many methods have been developed to meet the need building indole structures, among which the Fisher indolization still remains the most commonly used technique in industry. See: *Indoles*; Sundberg, R. J., Ed.; Academic: London, 1996; Sundberg, R. J. *Pyrroles and their Benzo Derivatives: Synthesis and Applications. In Comprehensive Heterocyclic Chemistry*. Notwithstanding this plethora of methodologies, regioselective formation of indoles with substitution at positions other than C-5 has proved to be challenging. The recently developed palladium-catalyzed indolization method by Larock et al (Larock, R. C.; Yum, E. K. J. Am. Chem. Soc. 1991, 113, 6689; Larock, R. C.; Yum, E. K.; Refyik, M. D. J. Org. Chem. 1998, 63, 7652) has provided one approach to the aforementioned regioselectivity issue. Larock reported that the best results could be obtained by reacting substituted ortho-iodolines with an excess of a suitable internal alkyne sodium or potassium acetate or carbonate base plus 1 equivalent of either LiCi or n-Bu$_4$NCl, and occasionally adding the ligand triphenylphosphine. Larock reported that this ligand was not essential for the palladium-catalyzed reaction. Larock also reported the use of triphenylphosphine as a ligand and did not find that it provided better indolization results.

This versatile "ligandless" heteroannulation of internal alkynes with 2-iodoanilines allows access to a variety of indoles which may not be readily available by conventional methods in terms of the degree of substitution and type of functionalization (eq. 1, Scheme 1). Replacing the iodoanilines with the corresponding 2-bromo or 2-chloro derivatives would be of significant practical and economical value from a cost and throughput perspective. However, Larock's protocol was not applicable to the indolization of acetylenes with 2-bromo or chloroanilines. The presence of iodide was postulated to have pronounced effect on the nature of the products in these alkyne insertion processes. (Larock, R. C.; Yum, E. K.; Refyik, M. D. *J. Org. Chem.* 1998, 63, 7652.) In addition, previous research on the reaction of ortho-palladation complexes with alkynes demonstrated the exclusive formation of multiple insertion products (eq. 2, Scheme 1). (Maassarani, F.; Pfeffer, M.; Borgne, G. L. *Organometallics* 1987, 6, 2029; (b) Maassarani, F.; Pfeffer, M.; Borgne, G. L., *Organometallics* 1987, 6, 2043; (c) Maassarani, F.; Pfeffer, M.; Spencer, J.; Wehman, E. *J. Organomet. Chem.* 1994, 466, 265.

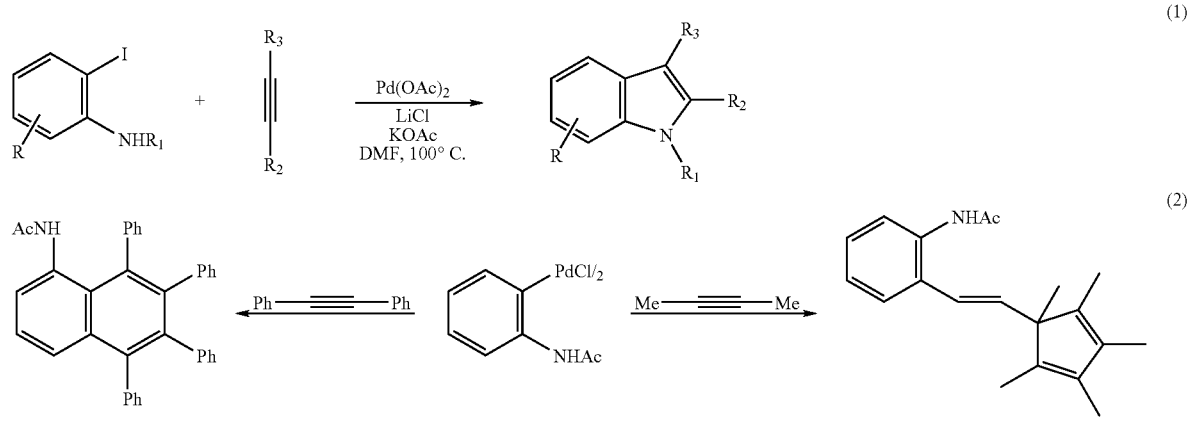

Scheme 1

There is a need in the art for conditions that are not substrate-specific and that could be used for performing palladium catalyzed indolizations on internal alkynes having a variety of substitutions at R$_2$ and R$_3$.

SUMMARY OF THE INVENTION

A method for making substituted indole compounds comprising the step of:
(a) reacting a 2-bromoaniline or 2-chloroaniline of formula (I)

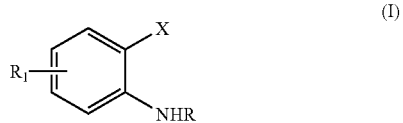

wherein:

X is Br or Cl,

R is H, $C_{1-8}$ alkyl, aryl, —C(O)$C_{1-6}$alkyl, —C(O)-aryl, —S(O)$_2C_{1-6}$alkyl or —S(O)$_2$aryl;

$R_1$ is $C_{1-6}$ alkyl, $C_{1-6}$ alkoxy, $CO_2H$, $CO_2M$ where M is selected from Na, K, Li, Mg,—$CO_2$ $C_{1-6}$ alkyl, $C_{1-6}$alkylHNC(O)—,

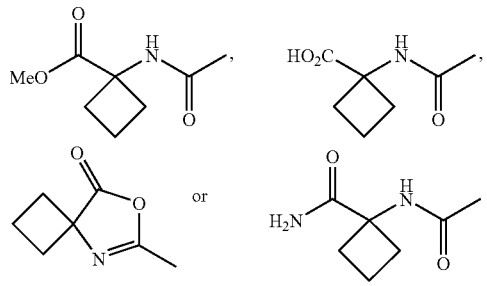

with a substituted acetylene of formula (II)

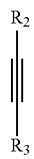

(II)

wherein $R_2$ is acyclic or cyclic alkyl, aryl, or heterocycle;

$R_3$ is: phenyl optionally substituted with F, Cl, alkyl, aryl, $CO_2C_{1-6}$ alkyl or carboxamide, or $R_3$ is heteroaryl selected from pyridine, pyrimidine, furan, thiophene, pyrrole and imidazole, optionally substituted with F, Cl, alkyl, aryl, $CO_2C_{1-6}$ alkyl or carboxamide, or $R_3$ is trialkysilyl, alkyl, alkoxy;

in the presence of a palladium catalyst, a ligand, and a base in a solvent to give a compound of formula (III);

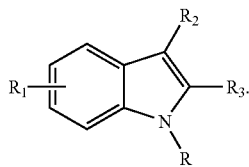

(III)

DESCRIPTION OF THE INVENTION

The present invention relates to the use of 2-bromo and 2-chloro aniline derivatives in an indolization reaction that uses an electron-rich palladium ligand.

It has been found that by using the appropriate ligand and reaction conditions in a palladium catalyzed coupling reaction, that 2-bromo- and 2-chloroaniline substrates can be used to obtain disubstituted indoles.

The 2-bromoaniline and 2-chloroaniline derivatives which can be used as starting materials in the present invention are typically significantly lower in cost than the corresponding 2-iodoaniline aniline derivatives. In addition, their molecular weights are much lower (MW: 185.6 for 2-chloroaniline, MW: 230.06 for 2-bromoaniline, and MW: 277.06 for the 2-iodoaniline), which would result in higher productivity (mass output) in the production of the indole intermediate.

The broadest embodiment of the invention provides a method for making substituted indole compounds comprising the step of:

(a) reacting a 2-bromoaniline or 2-chloroaniline of formula (I)

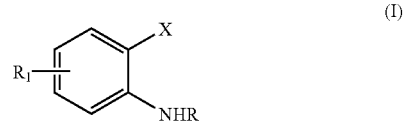

wherein:

X is Br or Cl,

R is H, $C_{1-8}$ alkyl, aryl, —C(O)$C_{1-6}$alkyl, —C(O)-aryl, —S(O)$_2C_{1-6}$alkyl or —S(O)$_2$aryl;

$R_1$ is $C_{1-6}$ alkyl, $C_{1-6}$ alkoxy, $CO_2H$, $CO_2M$ where M is selected from Na, K, Li, Mg,—$CO_2$ $C_{1-6}$ alkyl, $C_{1-6}$alkylHNC(O)—,

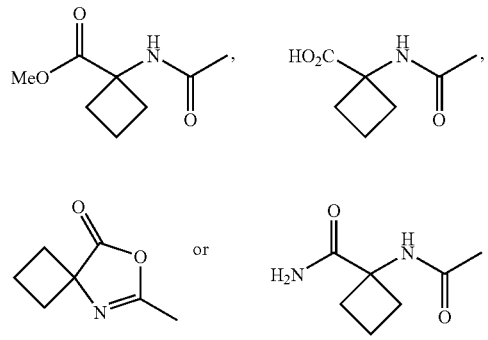

with a substituted acetylene of formula (II)

(II)

wherein $R_2$ is acyclic or cyclic alkyl, aryl, or heterocycle;

$R_3$ is: phenyl optionally substituted with F, Cl, alkyl, aryl, $CO_2C_{1-6}$ alkyl or carboxamide, or $R_3$ is heteroaryl selected from pyridine, pyrimidine, furan, thiophene, pyrrole and imidazole, optionally substituted with F, Cl, alkyl, aryl, $CO_2C_{1-6}$ alkyl or carboxamide, or $R_3$ is trialkysilyl, alkyl, alkoxy;

in the presence of a palladium catalyst, a ligand, and a base in a solvent to give a compound of formula (III);

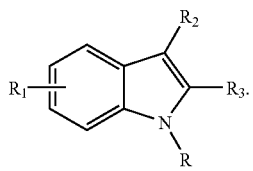
(III)

In another embodiment of the invention provides for the method immediately above wherein:
X: is Br or Cl;
R is H
$R_1$ is $C_{1-6}$ alkyl, $C_{1-6}$ alkoxy, $CO_2H$, $CO_2M$ where M is selected from Na, K, Li, Mg, $—CO_2C_{1-6}$ alkyl, $C_{1-6}$alkylHNC(O)—,

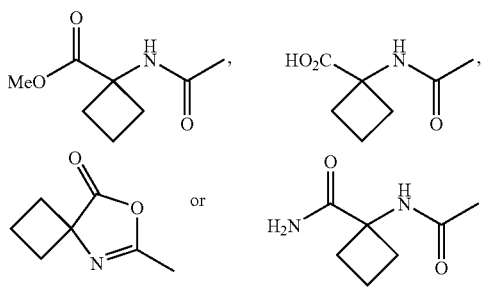

$R_2$ is acyclic or cyclic $C_{3-6}$ alkyl, $C_{6-8}$ aryl, or heterocycle,
$R_3$ is: phenyl optionally substituted with F, Cl, alkyl, aryl, $CO_2C_{1-6}$ alkyl or carboxamide, or $R_3$ is heteroaryl selected from pyridine, pyrimidine, furan, thiophene, pyrrole and imidazole, optionally substituted with F, Cl, alkyl, aryl, $CO_2C_{1-6}$ alkyl or carboxamide, or $R_3$ is trialkysilyl, alkyl, alkoxy.

Other embodiments of the invention include the process of the broadest embodiment wherein the ligand is selected from among:
a) 1,1'-bis(di-alkylphosphino)ferrocene,
b) trialkyphosphine, biphenyl dialkyphosphine.
c) 1,1'-bis(di-t-butylphosphino)ferrocene,
d) 1,1'-bis(di-iso-propylphosphino)ferrocene or tricyclohexylphosphine,
e) 2-(di-t-butylphosphino)-biphenyl,
f) 2-(di-t-butylphosphino)-2'-N,N-dimethylamino)biphenyl.

Another embodiment provides the broadest embodiment wherein the catalyst is selected from the list consisting of $Pd(OAc)_2$, $PdCl_2$, $PdBr_2$, $Pd_2(dba)_3$, $[Pd(ally)Cl]_2$, $Pd(CH_3CN)_2Cl_2$, $Pd(PhCN)_2Cl_2$, Pd/C, encapsulated Pd and $Pd(Cy_3P)_2Cl_2$.

Another embodiment provides the inventive process of the broadest embodiment wherein the base is selected from the list consisting of $K_2CO_3$, $KHCO_3$, $Na_2CO_3$, CsOAc, KOAc, $K_3PO_4$, $Cs_2CO_3$, 1,8-diazabicyclo[5.4.0]undec-7-ene (DBU), tetramethyl guanidine (TMG), $Bu_4N^+OAc^-$.

A preferred embodiment provides the inventive process of the broadest embodiment wherein the base is $K_2CO_3$.

A preferred embodiment provides the inventive process of the broadest embodiment wherein the solvent is 1-methyl-2-pyrrolidinone (NMP), N,N-dimethylformamide (DMF), N,N-dimethylacetamide (DMAc), 4,4-dimethyl-2-imidazoline (DMI), or xylenes.

In a further embodiment of the invention provides the inventive process of the broadest embodiment wherein the solvent is NMP or DMF.

A preferred embodiment provides the inventive process of the broadest embodiment wherein the the palladium catalyzed indolization reaction is run at a temperature between 110° C. and 140° C.

A preferred embodiment provides the inventive process of the broadest embodiment wherein the solvent is NMP, the base is $K_2CO_3$, the catalyst is $Pd(OAc)_2$ and the ligand is 1,1'-bis(di-t-butylphosphino)ferrocene or tri(cyclohexyl) phosphine.

Also provided in the invention are compounds of general formula I as described above that can be used to make intermediates internal alkynes having a variety of substitutions at $R_2$ and $R_3$.

General Synthetic Methods

In the synthetic schemes below, unless specified otherwise, all the substituent groups in the chemical formulas shall have the same meanings as in general Formula (I). The reactants used in the synthetic schemes described below may be obtained either as described herein, or if not described herein, are themselves either commercially available or may be prepared from commercially available materials by methods known in the art.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by High Pressure Liquid Chromatography (HPLC), if desired, and intermediates and products may be purified by chromatography on silica gel and/or by recrystallization.

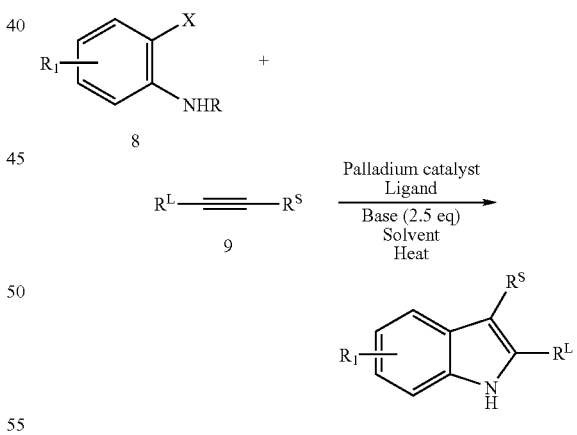

A suitable sized reaction flask equipped with a stirring and heating means are charged with palladium catalyst (0.5 to 10 mole %), ligand about 4 to 1 ratio to catalyst for monodentat or a 2 to 1 ratio for a bi-dentat ligand, a 2-bromoaniline or 2-chloroaniline compound (8) in about 1 equivalent wherein R, R1 and X are as defined herein, a suitable amount of solvent, and a substituted acetylene compound (9). L refers to the larger of the acetylene substituents and S refers to the smaller of the acetylene substituents. In some cases the substituents L and S may be the same and a base in more than 2 equivalents. The flask is then purged with inert gas. The reaction is typically heated to about 110 to 140° C., preferably about 110° C. and stirred until the reaction is completed. The mixture is then worked up using techniques commonly used in the art.

Chemical Nomenclature and Conventions Used

Terms not specifically defined herein should be given the meanings that would be given to them by one of skill in the art in light of the disclosure and the context. As used in the specification and appended claims, however, unless specified to the contrary, the following terms have the meaning indicated and the following conventions are adhered to.

The terms "alkyne" or "alkynyl" or "alkynyl group" mean a branched or straight-chain aliphatic hydrocarbon moiety containing at least one carbon-carbon triple bond. This term is exemplified by groups such as ethynyl, propynyl, n-butynyl, 2-butynyl, 3-methylbutynyl, n-pentynyl, heptynyl, octynyl, decynyl, and the like.

The terms "alkoxy" or "alkoxy group" mean a moiety of the formula AlkO-, where Alk is an alkyl group. This term is exemplified by groups such as methoxy, ethoxy, propoxy, isopropoxy, butoxy, sec-butoxy, t-butoxy, pentoxy, and the like.

The terms "alkyl" or "alkyl group" mean a branched or straight-chain saturated aliphatic hydrocarbon moiety. This term is exemplified by groups such as methyl, ethyl, n-propyl, isopropyl, n-butyl, n-pentyl, 1,1-dimethylethyl(tert-butyl), and the like.

The terms "heteroaryl" or "heteroaryl group" mean a stable aromatic 5- to 14-membered, monocyclic or polycyclic moiety which may comprise one or more fused or bridged ring(s), preferably 5- to 7-membered monocyclic or 7- to 10-membered bicyclic units, having from one to four heteroatoms in the ring(s) independently selected from nitrogen, oxygen, and sulfur, wherein any sulfur heteroatoms may optionally be oxidized and any nitrogen heteroatom may optionally be oxidized or quaternized. Unless otherwise specified, the heteroaryl ring may be attached at any suitable heteroatom or carbon atom which results in a stable structure and, if substituted, may be substituted at any suitable heteroatom or carbon atom which results in a stable structure. Exemplary and preferred heteroaryls include furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, triazinyl, indolizinyl, azaindolizinyl, indolyl, azaindolyl, diazaindolyl, dihydroindolyl, dihydroazaindoyl, isoindolyl, azaisoindolyl, benzofuranyl, furanopyridinyl, furanopyrimidinyl, furanopyrazinyl, furanopyridazinyl, dihydrobenzofuranyl, dihydrofuranopyridinyl, dihydrofuranopyrimidinyl, benzodioxolanyl, benzothienyl, thienopyridinyl, thienopyrimidinyl, thienopyrazinyl, thienopyridazinyl, dihydrobenzothienyl, dihydrothienopyridinyl, dihydrothienopyrimidinyl, indazolyl, azaindazolyl, diazaindazolyl, benzimidazolyl, imidazopyridinyl, benzthiazolyl, thiazolopyridinyl, thiazolopyrimidinyl, benzoxazolyl, oxazolopyridinyl, oxazolopyrimidinyl, benzisoxazolyl, purinyl, chromanyl, azachromanyl, quinolizinyl, quinolinyl, dihydroquinolinyl, tetrahydroquinolinyl, isoquinolinyl, dihydroisoquinolinyl, tetrahydroisoquinolinyl, cinnolinyl, azacinnolinyl, phthalazinyl, azaphthalazinyl, quinazolinyl, azaquinazolinyl, quinoxalinyl, azaquinoxalinyl, naphthyridinyl, dihydronaphthyridinyl, tetrahydronaphthyridinyl, pteridinyl, carbazolyl, acridinyl, phenazinyl, phenothiazinyl, and phenoxazinyl, and the like. Other preferred heteroaryls include pyridinyl, furanyl, pyrimidinyl, thiophene, pyrrole and imidazole.

The term "heterocycle" refers to a stable 4-8 membered (but preferably, 5 or 6 membered) monocyclic or 8–11 membered bicyclic heterocycle radical which may be either saturated or unsaturated, and is non-aromatic. Each heterocycle consists of carbon atoms and from 1 to 4 heteroatoms chosen from nitrogen, oxygen and sulfur. The heterocycle may be attached by any atom of the cycle, which results in the creation of a stable structure. Examples of "heterocycle" include radicals such as pyrrolinyl, pyrrolidinyl, pyrazolinyl, pyrazolidinyl, piperidinyl, morpholinyl, thiomorpholinyl, pyranyl, thiopyranyl, piperazinyl, indolinyl, azetidinyl, tetrahydropyranyl, tetrahydrothiopyranyl, tetrahydrofuranyl, hexahydropyrimidinyl, and hexahydropyridazinyl.

The terms "aryl" or "aryl group" mean an aromatic carbocyclic moiety of from 6 to 14 carbon atoms having a single ring (e.g., phenyl or phenylene) or multiple condensed rings (e.g., naphthyl or anthranyl). Unless otherwise specified, the aryl ring may be attached to any suitable carbon atom which results in a stable structure and, if substituted, may be substituted at any suitable carbon atom which results in a stable structure. Exemplary aryl groups include phenyl, naphthyl, anthryl, phenanthryl, indanyl, indenyl, biphenyl, and the like. Aryl may also be abbreviated as "Ar".

The terms "optional" or "optionally" mean that the subsequently described event or circumstances may or may not occur, and that the description includes instances where the event or circumstance occurs and instances in which it does not. For example, "optionally substituted cycloalkyl" means that the cycloalkyl moiety may or may not be substituted and that the description includes both substituted cycloalkyl and cyckloalkyl moieties having no substitution.

The term "substituted" means that any one or more hydrogens on an atom of a group or moiety, whether specifically designated or not, is replaced with a selection from the indicated group of substituents, provided that the atom's normal valency is not exceeded and that the substitution results in a stable compound. If a bond to a substituent is shown to cross the bond connecting two atoms in a ring, then such substituent may be bonded to any atom on the ring. When a substituent is listed without indicating the atom via which such substituent is bonded to the rest of the compound, then such substituent may be bonded via any atom in such substituent. Generally, when any substituent or group occurs more than one time in any constituent or compound, its definition on each occurrence is independent of its definition at every other occurrence. Such combinations of substituents and/or variables, however, are permissible only if such combinations result in stable compounds.

The yield of each of the reactions described herein is expressed as a percentage of the theoretical yield.

In one example of the inventive process, the reaction was conducted with methyl 3-amino-4-chloro-benzoate and 1-cyclopentyl-2-pyridinyl acetylene as the starting materials (Scheme 7). Suitable choices of ligand, base and solvent was important for obtaining satisfactory results as shown in Table 1. Several ligands were examined. It was found that the reaction proceeded smoothly to afford the desired indole product when using either ligand 4a, 4b or 5 in the presence of n-Bu$_4$N$^+$OAc$^-$. The major side-reaction was homocoupling of the arylchloride via double amination (entries 1–3). The proper choice of base, solvent, temperature, and concentration was important to minimize the formation of the amination byproduct and also maximize the desired regioselectivity. By using inorganic bases such as K$_2$CO$_3$, a cleaner reaction could be obtained than by using n-Bu$_4$N$^+$OAc$^-$ as base. When a ferrocene ligand such as bis(diisopropylphosphino)ferrocene was employed, in combination with K$_2$CO$_3$ as base, the indolization of 2-chloroaniline with the internal acetylene completed rapidly, providing the product in high purity and regioselectivity (entry 4). Addition of LiCl or LiI as additive did not improve the yield.

Instead, it slowed down the reaction (entries 5–6). With reduced catalyst loading (5 mol %), the reaction also proceeded smoothly and cleanly (entry 7). Changing the ratio of ligand to palladium acetate from 2:1 to 1:1 prolonged the reaction time (entry 8). Using K₂CO₃ as base, ligands 4a, 4b or 6 also afforded good results (entries 9–10). The wavelength used was 240 nm.

Scheme 7

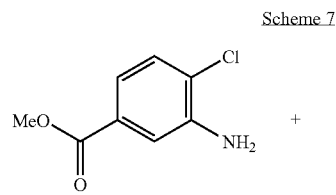

+

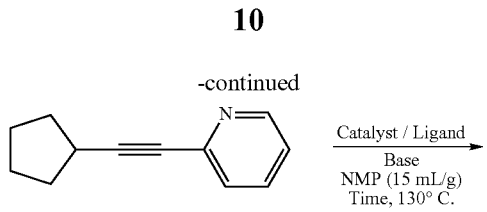

TABLE I

| Entry | (Scale) | Base (eq) | Catalyst | Time (h) | Result* |
|---|---|---|---|---|---|
| 1 | (100 mg) | n-Bu₄N⁺OAc⁻ (2.5 eq) | Pd(OAc)₂ (10%) 2-(Di-t-butylphosphino)-biphenyl (40%) | 4 | Complete conversion of starting material, giving 45 area % product and 33 area % byproduct. |
| 2 | (100 mg) | n-Bu₄N⁺OAc⁻ (2.5 eq) | Pd(OAc)₂ (10%) 1,1'-Bis(diphenylphosphino)ferrocene(20%) | 3 | Ratio of the desired product to starting material (cholroaniline) was 5:1, about 35 area % unknown impurities. The ratio of the regioisomers was 9:1. |
| 3 | (200 mg) | n-Bu₄N⁺OAc⁻ (2.5 eq) | Pd(OAc)₂ (10%) 1,1'-Bis(di-i-propylphosphino)ferrocene(20%) | 14 | Complete conversion of the starting material, about 35 area % of unknown impurities. The ratio of the regioisomers was 9:1. 28% isolated yield was obtained through column chromatography for two steps. |
| 4 | (100 mg) | K₂CO₃ (2.5 eq) | Pd(OAc)₂ (10%) 1,1'-Bis(di-i-propylphosphino)ferrocene(20%) | 3 | Complete conversion of the starting material. The desired product was formed in 88 area % purity. The ratio of the regioisomers was 20:1. |
| 5 | (100 mg) | K₂CO₃ (2.5 eq) LiCl (1 eq) | Pd(OAc)₂ (10%) 1,1'-Bis(di-i-propylphosphino)ferrocene(20%) | 5 | Ratio of the desired product to the starting material was 14:1. The ratio of the regioisomers was 19:1. |
| 6 | (100 mg) | K₂CO₃ (2.5 eq) LiI (1 eq) | Pd(OAc)₂ (10%) 1,1'-Bis(di-i-propylphosphino)ferrocene(20%) | 5 | The ratio of the desired product to the starting material was 1.6:1. |
| 7 | (100 mg) | K₂CO₃ (2.5 eq) | Pd(OAc)₂ (5%) 1,1'-Bis(di-i-propylphosphino)ferrocene(10%) | 14 | The ratio of the desired product to the starting material was 5:1. The ratio of regioisomers was 18:1. |
| 8 | (100 mg) | K₂CO₃ (2.5 eq) | Pd(OAc)₂ (5%) 1,1'-Bis(di-i-propylphosphino)ferrocene(6%) | 14 | The ratio of the desired product to the starting material was 2.5:1. The ratio of regioisomers was 19:1. |
| 9 | (100 mg) | K₂CO₃ (2.5 eq) | Pd(OAc)₂ (5%) 2-(Di-t-butylphosphino)-biphenyl (10%) | 14 | Complete conversion of the starting material, with about 20 area % impurities. The ratio of the regioisomers was 20:1. |
| 10 | (100 mg) | K₂CO₃ (2.5 eq) | Pd(OAc)₂ (5%) Tricyclohexylphosphine (10%) | 14 | The ratio of the desired product to the starting material was 4:1. Ratio of the regioisomers was 18:1. |

*Ratios of product were measured by HPLC analysis

An example of the indolization reaction using a substituted bromoaniline is illustrated in Scheme 8. Under the same conditions used for the indolization of the corresponding 2-chloroaniline derivative, the reaction of the 2-bromoaniline with the acetylene was highly efficient based on yield and conversion. The reaction was clean and was completed within 5 hours in the presence of 10 mol % of palladium acetate within 5 hours. No major byproducts were observed. After methylation of the N—H indole product, the N-Me product was obtained with 94 area % purity in the reaction mixture. The ratio of the regioisomers was 19:1. The product was obtained in 87% yield following flash chromatography.

Scheme 8

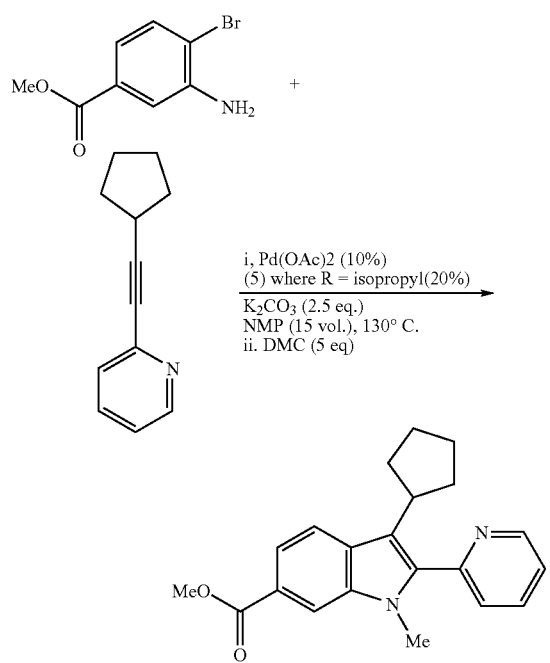

The reaction was further studied as shown in Scheme 9 and the results are summarized in Table 2.

Scheme 9

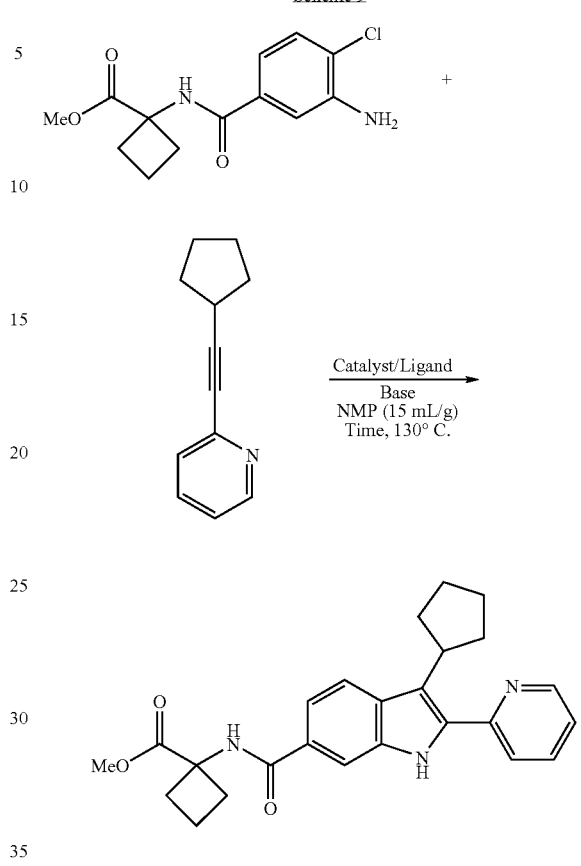

By employing the same conditions used in Scheme 8, the reaction illustrated in Scheme 9 proceeded more slowly. Extended reaction time was needed for complete conversion. Similar results were observed whether using ligands 4a, 4b, 5 or 6. Among all of the ligands examined, 5 (R=t-butyl) provided the best result, with minimal homo-coupling of the 2-chloroaniline. The results are described in Table II.

TABLE II

| (Scale) | Catalyst | Base | Solvent | Result* |
|---|---|---|---|---|
| (1 g) | Pd(OAc)$_2$ (5%) Dippf (10%) | Cs$_2$CO$_3$ (2.5 eq) | o-xylene (15 v) | Trace amount of product, chloroaniline was decomposed after longer reaction time (>24 h) |
| (200 mg) | Pd(OAc)$_2$ (5%) 2-(Di-t-butylphosphino)-biphenyl (10%) | K$_2$CO$_3$ (2.5 eq) | NMP (5 v) | 100% conversion after 19 h; amination byproduct was also observed. |
| (500 mg) | Pd(OAc)$_2$ (3%) 2-(Di-t-butylphosphino)-biphenyl (6%) | K$_2$CO$_3$ (2.5 eq) | NMP (5 v) | 14 hr, 50% conversion; 71 A % purity |
| (200 mg) | Pd(OAc)$_2$ (5%) PCy$_3$ (20%) | K$_2$CO$_3$ (2.5 eq) | NMP (5 v) | 71% conversion after 19 h; no amination by product; ratio of the regioisomers was 20:1 |
| (500 mg) | Pd(OAc)$_2$ (3%) PCy$_3$ (12%) | K$_2$CO$_3$ (2.5 eq) | NMP (5 v) | 14 h, 75% conversion; 90 A % purity |
| (200 mg) | Pd(OAc)$_2$ (5%) Dippf (10%) | K$_2$CO$_3$ (2.5 eq) | NMP (5 v) | 47% conversion after 19 h; no amination byproduct; |
| (200 mg) | Pd(OAc)$_2$ (5%) Dppf (10%) | K$_2$CO$_3$ (2.5 eq) | NMP (5 v) | 67% conversion after 19 h; no amination byproduct; ratio of the regioisomers was 21:1 |

TABLE II-continued

| (Scale) | Catalyst | Base | Solvent | Result* |
|---|---|---|---|---|
| (200 mg) | Pd(OAc)$_2$ (5%)<br>BINAP (10%) | K$_2$CO$_3$<br>(2.5 eq) | NMP<br>(5 v) | 73% conversion after 19 h;<br>no amination byproduct;<br>Significant amount of nonpolar<br>byproduct was observed. |
| (200 mg) | Pd(OAc)$_2$ (5%)<br>2-dicyclohexylphosphino-<br>2'-(N,N-<br>dimethylamino)biphenyl<br>(10%) | K$_2$CO$_3$<br>(2.5 eq) | NMP<br>(5 v) | 4 hr, 100% conversion, 87 A % purity |
| (500 mg) | Pd(OAc)$_2$ (3%)<br>2-dicyclohexylphosphino-<br>2'-(N,N-<br>dimethylamino)biphenyl<br>(6%) | K$_2$CO$_3$<br>(2.5 eq) | NMP<br>(5 v) | 14 hr, 100% conversion, 85 A %<br>purity |
| (200 mg) | Pd(OAc)$_2$ (5%)<br>dppe (10%) | K$_2$CO$_3$<br>(2.5 eq) | NMP<br>(5 v) | 19 hr, 62% conversion, >90 A %<br>purity |
| (200 mg) | Pd(OAc)$_2$ (5%)<br>dppp (10%) | K$_2$CO$_3$<br>(2.5 eq) | NMP<br>(5 v) | 19 hr, 87% conversion, >95 A %<br>purity |
| (200 mg) | Pd(OAc)$_2$ (5%)<br>dppb (10%) | K$_2$CO$_3$<br>(2.5 eq) | NMP<br>(5 v) | 19 hr, 80% conversion, >95 A %<br>purity |
| (500 mg) | Pd(OAc)$_2$ (3%)<br>2-(Di-<br>cyclohexylphosphino)-<br>biphenyl (6%) | K$_2$CO$_3$<br>(2.5 eq) | NMP<br>(5 v) | 14 hr, 41% conversion;<br><70 A % purity |
| (500 mg) | Pd(OAc)$_2$ (3%)<br>$^t$Bu$_3$P (12%) | K$_2$CO$_3$<br>(2.5 eq) | NMP<br>(5 v) | 14 h, 56% conversion; 62 A % purity |
| (500 mg) | Pd(OAc)$_2$ (3%)<br>Dtbpf (6%) | K$_2$CO$_3$<br>(2.5 eq) | NMP<br>(5 v) | 32 hr, 91% conversion; 92 A % purity. |
| (500 mg) | Pd(OAc)$_2$ (3%)<br>TangPhos (6%) | K$_2$CO$_3$<br>(2.5 eq) | NMP<br>(5 v) | 32 hr, 77% conversion; 87 A % purity. |
| (500 mg) | Pd(OAc)$_2$ (3%)<br>DuPhos (6%) | K$_2$CO$_3$<br>(2.5 eq) | NMP<br>(5 v) | 32 hr, 29% conversion; 35 A % purity. |

*Ratio was determined using HPLC analysis

The starting material was readily prepared by a two-step process from the commercially available 3-nitro-4-chloro-6-benzoyl chloride.

Ligands—Suitable ligands that can be used in the invention include highly reactive ligands such as the biphenyl type Buchwald type biphenyl ligands (4a, 4b) ferrocene type ligands (5) or tricyclohexylphosphine ligands (6).

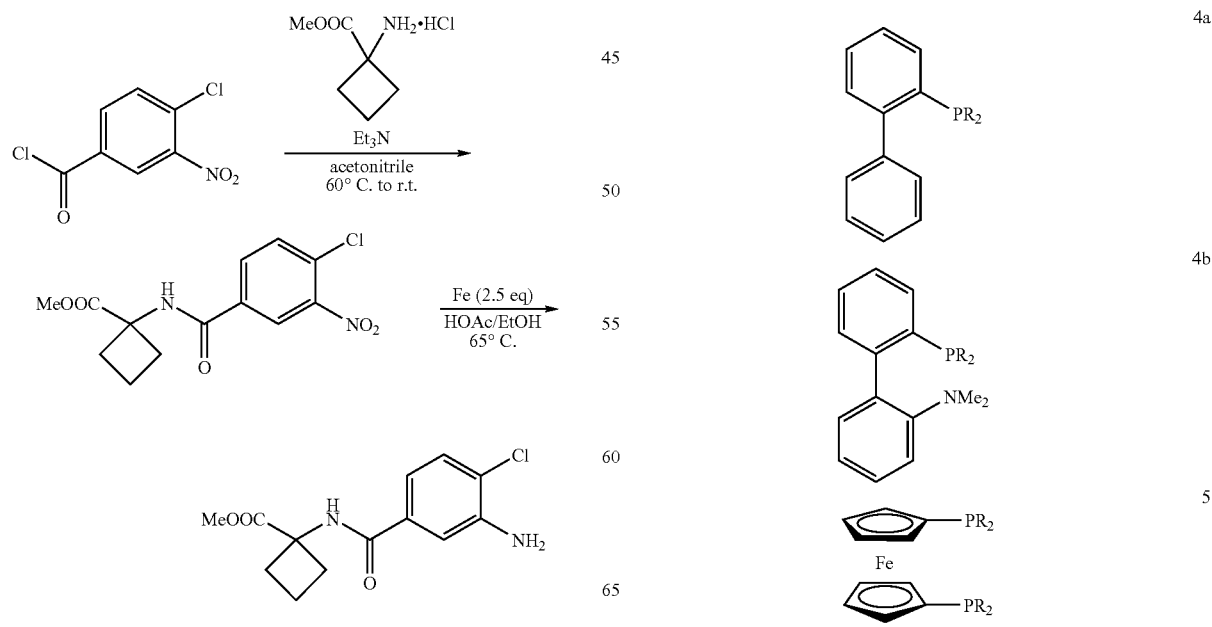

15

-continued

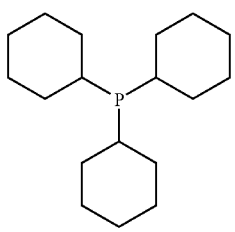
6 where in (4a) and (4b) R is cyclohexyl, or t-butyl and in (5) R is isopropyl, or t-butyl.

Catalysts—a number of catalysts can be used in inventive process embodiment provides the inventive process including Pd(OAc)$_2$, PdCl$_2$, PdBr$_2$, Pd$_2$(dba)$_3$, [Pd(ally)Cl]$_2$, Pd(CH$_3$CN)$_2$Cl$_2$, Pd(PhCN)$_2$Cl$_2$, Pd/C, encapsulated Pd and Pd(Cy$_3$P)$_2$Cl$_2$.

Bases—suitable bases that can be used in the inventive process include selected from the list consisting of K$_2$CO$_3$, KHCO$_3$, Na$_2$CO$_3$, CsOAc, KOAc, K$_3$PO$_4$, Cs$_2$CO$_3$, 1,8-diazabicyclo[5.4.0]undec-7-ene (DBU), tetramethyl guanidine (TMG), Bu$_4$N$^+$OAc$^-$.

Solvents—suitable solvents that can be used in the inventive process include 1-methyl-2-pyrrolidinone (NMP), N,N-dimethylformamide (DMF), N,N-dimethylacetamide (DMAc), 4,4-dimethyl-2-imidazoline (DMI), or xylenes.

SYNTHETIC EXAMPLES

In order for the present invention to be more fully understood, the following examples are set forth. These examples are for the purpose of illustrating embodiments of this invention, and are not to be construed as limiting the scope of the invention in any way since, as recognized by one skilled in the art, particular reagents or conditions could be modified as needed for individual compounds. Starting materials used are either commercially available or readily prepared from commercially available materials by those skilled in the art.

Synthetic Examples

All reactions were carried out in dried glassware sealed with rubber septa under an inert atmosphere of argon or nitrogen. All commercial materials were used without further purification. Analytical high performance liquid chromatography (HPLC) was performed on Agilent 1100 Series equipped with a UV detector and Eclipse XDB-C8 4.6×150 mm 5 μm column. Analytical thin layer chromatography (TLC) was visualized by ultraviolet light (254 nm) and treatment with phosphomolybdic acid stain followed by gentle heating. Chemical yields refer to pure isolated substances. Purification of products was accomplished by flash chromatography using Isolute SPE columns pre-packed with Flash Si II purchased from Isolute. $^1$H and $^{13}$C NMR were recorded using a Bruker 400. Chemical shifts are reported in ppm. The following abbreviations were used to designate chemical shift multiplicities: s=singlet, d=doublet, t=triplet, q=quartet, h=heptet, m=multiplet, br=broad. High resolution mass spectra were obtained on a VG70-250S (double focusing) mass spectrometer at 70 eV.

Example 1

Synthesis of 5-methyl-2-phenyl-3-propylindole (1a)

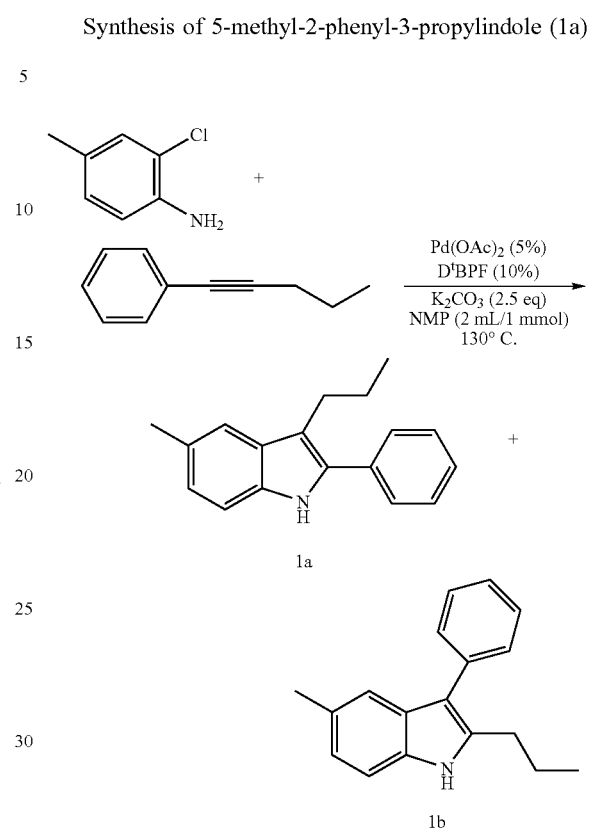

Pd(OAc)$_2$ (11 mg, 0.05 mmol), 1,1'-bis(di-t-butylphosphino)ferrocene (D$^t$BPF) (47 mg, 0.1 mmol) and K$_2$CO$_3$ (346 mg, 2.5 mmol) were added to an oven-dried reaction vial. The vial was purged with argon. 2-Chloro-4-methylaniline (123 μL, 1 mmol), 1-phenyl-1-pentyne (192 μL, 1.2 mmol) and 1-methyl-2-pyrrolidinone (NMP) (2 mL) were added via syringe. The reaction was heated to 130° C., stirred at the same temperature and monitored by HPLC. The reaction was complete after 4 h. The ratio of the desired regioisomer (1a) to the by-product (1b) was 91:9. The mixture was filtered through a pad of diatomaceous earth. The cake was washed with EtOAc. The combined organic filtrate was washed with water and brine, dried over MgSO$_4$, filtered and concentrated to give a brown residue. The product was purified via column chromatography.

$^1$H NMR (300 MHz, CDCl$_3$) δ 7.90 (s, 1H), 7.60–7.00 (m, 8H), 2.80 (t, J=7.0 Hz, 2H), 2.48 (s, 3H), 1.75–1.64 (m, 2H), 0.86 (t, J=7.0 Hz, 3H); LC-MSD (API-ES, positive) m/z=250 (M+H$^+$).

Example 2

The following examples illustrate the general applicability of the palladium catalyzed indolization.

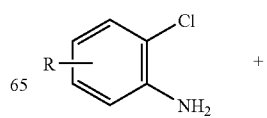

-continued

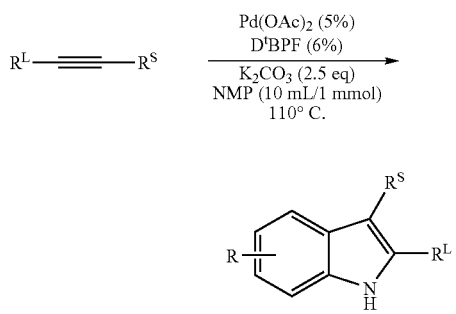

3-Ethyl-2-isopropenyl-5-methyl-1H-indol

A 100 ml reaction flask equipped with a stirring bar and thermocouple are charged with Pd(OAc)$_2$ (56 mg, 0.25 mmol), D$^t$BPF (142 mg, 0.3 mmol), 2-chloro-4-methylaniline (0.71 g, 5 mmol), 2-methyl-1-hexen-3-yne (0.94 g, 10 mmol), K$_2$CO$_3$ (1.73 g, 12.5 mmol) and DMF (50 mL). The flask was purged with argon. The reaction was heated to 110° C. and stirred overnight. The reaction was complete after 20 h at 110° C. The mixture was filtered through a layer of diatomaceous earth and washed with EtOAc (10 mL). The filtrate was diluted with water (50 mL), extracted with EtOAc (100 mL×3). The combined organic phase was washed with water (50 mL×4) and brine, dried over MgSO$_4$, filtered and concentrated to give a dark brown residue. The product was purified via chromatography on silica gel (hexane/EtOAc 50/1). The desired product was obtained as an off-white solid (0.6 g, 60%).

The following compounds were made using the same procedure, starting with the appropriate substituted aniline and acetylene intermediates:

5-Methyl-2-phenyl-3-propyl-1H-indole

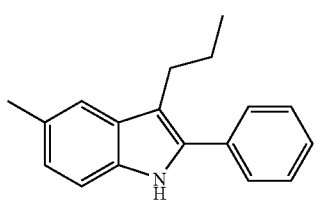

Yield: 76%; off-white solid; m.p. 120–123° C.; $^1$H NMR (300 MHz, CDCl$_3$) δ 7.90 (s, 1H), 7.60–7.40 (m, 5H), 7.34–7.29 (m, 1H), 7.21–7.18 (m, 1H), 7.01–6.98 (m, 1H), 2.80 (t, J=7.0 Hz, 2H), 2.48 (s, 3H), 1.75–1.64 (m, 2H), 0.86 (t, J=7.0 Hz, 3H); $^{13}$C NMR (100 MHz, CDCl$_3$) δ 134.31, 134.27, 133.67, 129.62, 128.81, 128.67, 127.92, 127.38, 123.78, 119.05, 113.60, 110.48, 26.80, 24.30, 21.66, 14.53; LC-MSD (API-ES, positive) m/z=250 (M+H$^+$); HR-MS Calcd 249.1517, found 249.1515.

3-Cyclopentyl-5-methyl-2-pyridin-2-yl-1H-indole

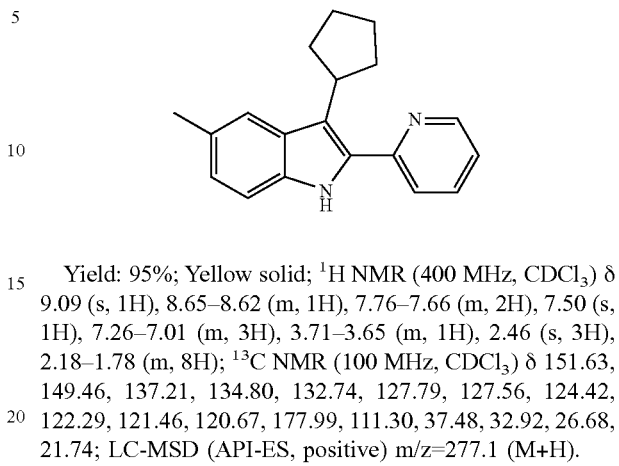

Yield: 95%; Yellow solid; $^1$H NMR (400 MHz, CDCl$_3$) δ 9.09 (s, 1H), 8.65–8.62 (m, 1H), 7.76–7.66 (m, 2H), 7.50 (s, 1H), 7.26–7.01 (m, 3H), 3.71–3.65 (m, 1H), 2.46 (s, 3H), 2.18–1.78 (m, 8H); $^{13}$C NMR (100 MHz, CDCl$_3$) δ 151.63, 149.46, 137.21, 134.80, 132.74, 127.79, 127.56, 124.42, 122.29, 121.46, 120.67, 177.99, 111.30, 37.48, 32.92, 26.68, 21.74; LC-MSD (API-ES, positive) m/z=277.1 (M+H).

5-Methyl-2,3-dipropyl-1H-indole

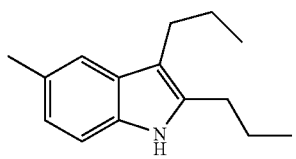

Yield: 82%; Yellow solid; Compound is unstable and easily decomposed after column; $^1$H NMR (400 MHz, CDCl$_3$) δ 7.55 (s, 1H), 7.29 (d, J=0.5 Hz, 1H), 7.10 (d, J=8.5 Hz, 1H), 6.91 (dd, J=8.5, 0.5 Hz, 1H), 2.65–2.61 (m, 4H), 2.44 (s, 3H), 1.64–1.62 (m, 4H), 0.97–0.93 (m, 6H); $^{13}$C NMR (100 MHz, CDCl$_3$) δ 134.16, 132.34, 127.79, 126.71, 120.95, 116.92, 110.38, 108.67, 26.93, 25.08, 22.90, 21.95, 20.33, 13.06, 12.74; LC-MSD (API-ES, positive) m/z=216.1 (M+H).

5-Methyl-2,3-diphenyl-1H-indole

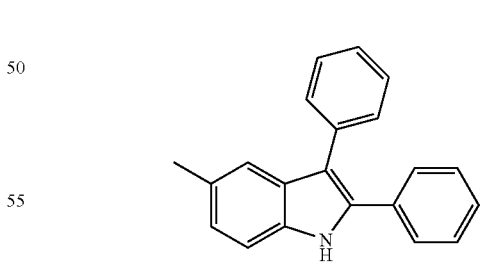

Yield: 86%; Off-White solid; m.p. 153–155° C.; $^1$H NMR (400 MHz, CDCl$_3$) δ 8.15 (s, 1H), 7.48–7.28 (m, 12H), 7.12–7.09 (m, 1H), 2.44 (s, 3H); $^{13}$C NMR (100 MHz, CDCl$_3$) δ 135.22, 134.19, 134.18, 132.80, 130.19, 129.75, 129.00, 128.65, 128.50, 128.07, 127.57, 126.15, 124.30, 119.22, 114.57, 110.54, 21.54; LC-MSD (API-ES, positive) m/z=284.1 (M+H); HR-MS Calcd 283.1361, found 283.1353.

3-Ethyl-2-isopropenyl-5-methyl-1H-indole

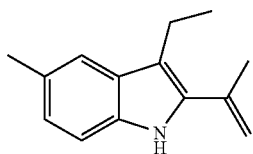

Yield: 60%; Off-white solid; ¹H NMR (400 MHz, CDCl₃) δ 7.71 (s, 1H), 7.35 (s, 1H), 7.18 (d, J=8.0 Hz, 1H), 6.99 (d, J=8.0 Hz, 1H), 5.23 (br s, 1H), 5.18–5.17 (m, 1H), 2.85 (q, J=7.5 Hz, 2H), 2.45 (s, 3H), 2.20 (s, 3H), 1.26 (t, J=7.5 Hz, 3H); ¹³C NMR (100 MHz, CDCl₃) δ 136.34, 134.37, 133.56, 129.22, 128.47, 123.87, 118.56, 115.44, 113.83, 110.23, 22.46, 21.58, 18.10, 15.58; LC-MSD (API-ES, positive) m/z=200.2 (M+H).

5-Methyl-3-phenyl-2-trimethylsilanyl-1H-indole

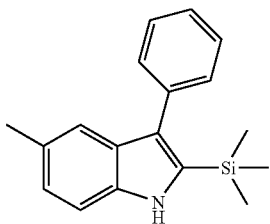

Yield: 63%; yellow oil; ¹H NMR (400 MHz, CDCl₃) δ 8.03 (s, 1H), 7.47–7.27 (m, 7H), 7.05–7.02 (m, 1H), 2.40 (s, 3H), 0.19 (s, 9H); ¹³C NMR (100 MHz, CDCl₃) δ 137.10, 136.60, 134.51, 130.76, 129.54, 129.22, 128.43, 127.65, 126.87, 124.77, 119.36, 110.83, 21.85, 0.00; LC-MSD (API-ES, positive) m/z=280.1 (M+H).

3-Cyclopentyl-2-pyridin-2-yl-6-trifluoromethyl-1H-indole

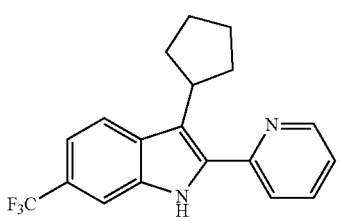

Yield: 93%; yellow solid; ¹H NMR (400 MHz, CDCl₃) δ 10.28 (s, 1H), 8.64 (d, J=4.0 Hz, 1H), 7.82–7.72 (m, 3H), 7.57 (s, 1H), 7.28–7.22 (m, 2H), 3.75–3.66 (m, 1H), 2.16–1.97 (m, 6H), 1.86–1.79 (m, 2H); ¹³C NMR (100 MHz, CDCl₃) δ 150.28, 149.00, 136.31, 134.74, 134.60, 128.97, 124.60 (q, J=270 Hz), 123.88 (q, J=32 Hz), 122.25, 121.79, 120.86, 118.14, 114.74 (q, J=3 Hz), 108.50 (q, J=4 Hz), 36.75, 32.56, 26.15; LC-MSD (API-ES, positive) m/z=331.0 (M+H).

3-Methyl-2-phenyl-6-trifluoromethyl-1H-indole

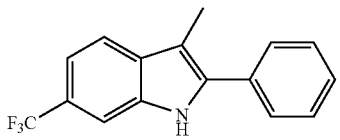

Yield: 65%; yellow solid; ¹H NMR (400 MHz, CDCl₃) δ 8.18 (s, 1H), 7.71 (d, J=8.5 Hz, 1H), 7.60 (s, 1H), 7.48–7.47 (m, 4H), 7.36–7.31 (m, 2H), 2.54 (s, 3H); ¹³C NMR (100 MHz, CDCl₃) δ 135.69, 133.53, 131.49, 131.18, 127.94, 126.96, 126.80, 125.62, 123.23 (q, J=30 Hz), 118.23, 115.20 (q, J=3 Hz), 107.86, 107.15 (q, J=4 Hz), 8.52.

2-Methyl-3-phenyl-6-trifluoromethyl-1H-indole

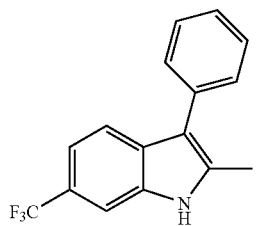

Yield: 9%; yellow oil; ¹H NMR (400 MHz, CDCl₃) δ 8.18 (s, 1H), 7.71 (d, J=8.5 Hz, 1H), 7.60 (s, 1H), 7.48–7.47 (m, 4H), 7.36–7.31 (m, 2H), 2.54 (s, 3H); ¹³C NMR (100 MHz, CDCl₃) δ 134.53, 134.34, 134.06, 130.18, 129.40, 128.66, 126.29, 125.26 (q, J=269 Hz), 123.53 (q, J=32 Hz), 119.03, 116.73 (q, J=3 Hz), 114.99, 107.78 (q, J=5 Hz), 12.66.

2-(3-Ethyl-1H-indol-2-yl)-propan-2-ol

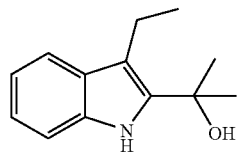

Yield: 60%; yellow oil; ¹H NMR (400 MHz, CDCl₃) δ 8.44 (s, 1H), 7.54 (d, J=7.5 Hz, 1H), 7.31 (d, J=8.5 Hz, 1H), 7.16–7.06 (m, 2H), 2.83 (q, J=7.5 Hz, 2H), 2.08 (s, 1H), 1.70 (s, 6H), 1.26 (t, J=7.5 Hz, 3H); ³C NMR (100 MHz, CDCl₃) δ 137.76, 132.16, 127.65, 119.73, 117.37, 116.87, 109.42, 109.13, 69.28, 29.49, 16.45, 14.32.

2,3-Diphenyl-1H-indole

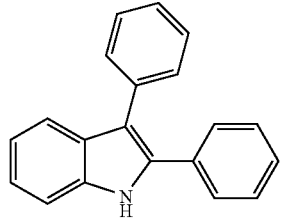

Yield: 97%; yellow solid; ¹H NMR (400 MHz, CDCl₃) δ 8.13 (s, 1H), 7.67 (d, J=8.0 Hz, 1H), 7.44–7.18 (m, 13H); ¹³C NMR (100 MHz, CDCl₃) δ 135.70, 134.88, 133.92, 132.49, 129.99, 128.56, 128.52, 128.37, 128.02, 127.53, 126.07, 122.54, 120.27, 119.53, 114.85, 110.75.

3-Cyclopentyl-6-methoxy-2-pyridin-2-yl-1H-indole

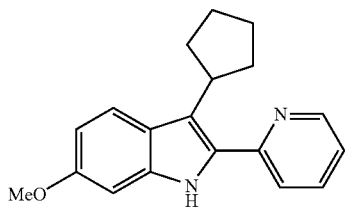

¹H NMR (300 MHz, DMSO-d₆) δ 11.1 (s, 1H), 8.66 (d, J=4.5 Hz, 1H), 7.87 (dt, J=8.0, 2.0 Hz, 1H), 7.66 (br d, J=8.0 Hz, 1H), 7.50 (d, J=9.0 Hz, 1H), 7.28 (dd, J=7.5, 5.0 Hz, 1H), 6.90 (d, J=2.0 Hz, 1H), 6.64 (dd, J=9.0, 2.5 Hz, 1H), 3.92–3.87 (m, 1H), 3.77 (s, 3H), 1.99–1.85 (m, 6H), 1.72–1.69 (m, 2H).

Example 3

Synthesis of 3-cyclopentyl-1-methyl-2-pyridin-2-yl-1H-indole-6-carboxylic acid methyl ester (13)

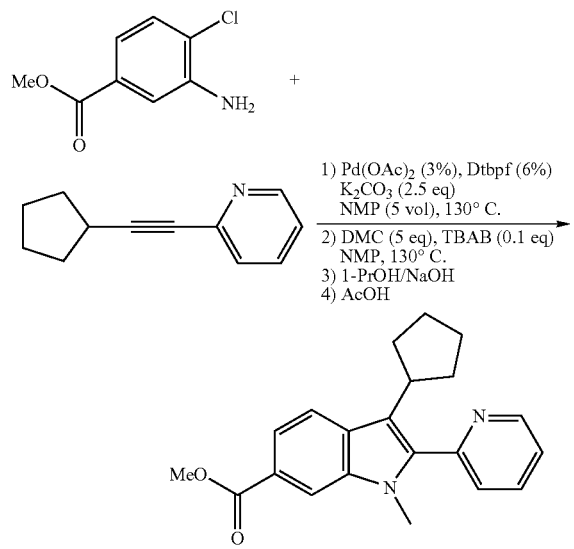

A 100 mL three neck flask equipped with a thermocouple, condenser and stir bar was purged with argon. 3-Amino-4-chlorobenzoic acid methyl ester (5.0 g, 26.94 mmol), 2-cyclopentylethynyl-pyridine (5.528 g, 32.33 mmol), Pd(OAc)₂ (181 mg, 0.81 mmol), DᵗBPF (767 mg, 1.62 mmol), K₂CO₃ (9.29 g, 67.35 mmol) and NMP (25 mL) were then charged. The reaction was heated to 130° C. and monitored by HPLC. The reaction was complete after 6 hours.

The reaction was cooled to room temperature. DMC (11.4 mL, 134.69 mmol) and tetrabutylammonium bromide (TBAB) (0.868 g, 2.69 mmol) were added. The mixture heated to 130° C. HPLC showed less than 3% starting material remaining after 4.5 h. The mixture was filtered through a pad of diatomaceous earth. The black cake was washed with i-PrOAc (50 mL). Solution yield of this mixture was 78%.

The crude product residue was dissolved in i-PrOAc (50 mL). The solution was washed with 0.3 N aqueous HCl three times (20 mL, then 2×15 mL). The organic phase was concentrated under vacuum. Propanol, water and 50% NaOH were added to the above residue. The reaction was heated to 90° C. for 1 h. HPLC showed that the reaction was complete. After the mixture was cooled to 50–60° C., diatomaceous earth and activated carbon were added. The mixture was stirred at 50° C. for 30 min and filtered to a 100 mL three neck flask through a pad of diatomaceous earth. The wet cake was washed with 18 mL of water/1-propanol 9/1. The mixture was then heated to 50° C. Acetic acid was added dropwise at this temperature. Precipitation was observed upon the addition. The suspension was then heated to reflux and held for 30 min. The mixture was slowly cooled to room temperature for 2 hours. The precipitate that formed was filtered. The wet cake was washed with 10 mL 1-propanol/water (2:1). The yellow solid was dried under vacuum for 2 days. 5.6 g product was obtained. The yield was 62% for three steps with 99.32 A % purity. ¹H NMR (300 MHz, DMSO-d⁶) δ 8.80 (d, J=3.0 Hz, 1H), 8.14 (s, 1H), 8.00 (m, 1H), 7.77 (d, J=6.0 Hz, 1H), 7.69 (d, J=9.0 Hz, 1H), 7.59 (d, J=6.0 Hz, 1H), 7.50 (m, 1H), 3.89 (s, 3H), 3.70 (s, 3H), 3.17–3.11 (m, 1H), 1.90–1.60 (m, 8H).

Example 4

Synthesis of 1-[(3-Cyclopentyl-1-methyl-2-pyridin-2-yl-1H-indole-6-carbonyl)-amino]-cyclobutanecarboxylic acid methyl ester (14)

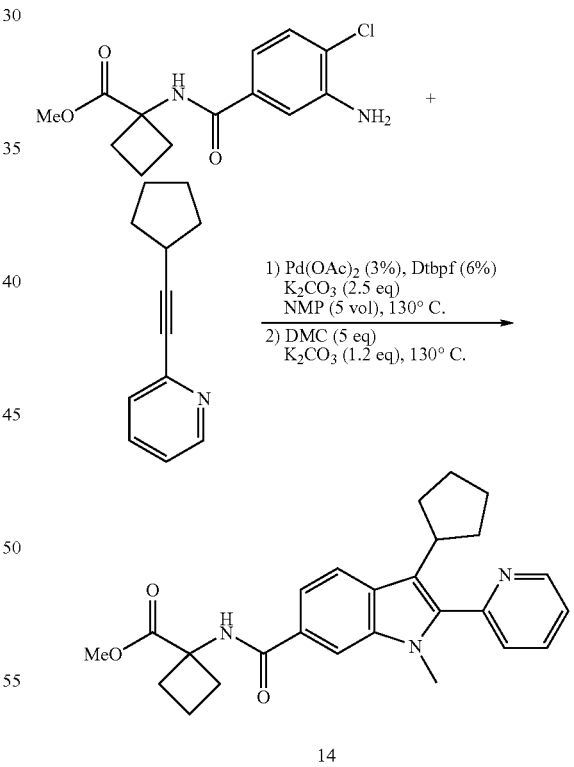

A 100 mL three neck flask equipped with thermocouple, condenser and stir bar was purged with argon. 1-(3-amino-4-chloro-benzoylamino)cyclobutanecarboxylic acid methyl ester (5 g, 17.69 mmol), palladium acetate (0.119 g, 0.53 mmol), 1,1'-bis(di-t butylphosphino)ferrocene (0.503 g, 1.06 mmol) and potassium carbonate (6.101 g, 44.21 mmol) were charged into the flask. 2-Cyclopentylethynyl-pyridine (3.629 g, 21.22 mmol) and NMP (25 mL) were added via syringe. The reaction was heated to 130° C. and stirred at the same temperature. The reaction was monitored by HPLC.

After cooling to room temperature, DMC (7.5 mL, 88.43 mmol) and K$_2$CO$_3$ (2.93 g, 21.22 mmol) were added. The reaction was stirred at 135° C. for 6 h. Additional DMC (3 mL) was added. The reaction was stirred for another 4 h.

The mixture was filtered through a pad of diatomaceous earth. The black cake was washed with ethyl acetate (50 mL, 10 v). The black solution was washed with 0.3 N HCl solution (30 mL). The product precipitated. After vacuum filtration, 3.02 g (97.84% purity at 248 nm) light yellow solid was obtained. A second crop 0.66 g (97.84 purity) was obtained as an off-white solid. Isolated yield was 48%.

$^1$H NMR (300 MHz, CDCl$_3$) δ 8.72 (m, 1H), 7.99 (s, 1H), 7.80–7.28 (m, 5H), 6.90 (s, 1H), 3.81 (s, 3H), 3.73 (s, 3H), 3.25–3.10 (m, 1H), 2.80–2.46 (m, 4H), 2.20–1.60 (m, 10H).

The following compound was prepared from 3-amino-4-chlorobenzoic acid methyl ester using the procedure described in the above example:

3-Cyclopentyl-1-methyl-2-pyridin-2-yl-1H-indole-6-carboxylic acid methyl ester

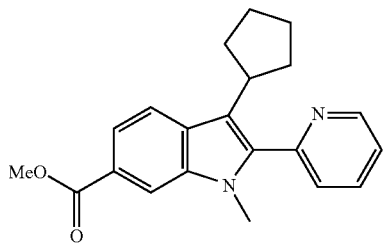

$^1$H NMR (300 MHz, DMSO-d$_6$) δ 8.81–8.80 (m, 1H), 8.14 (s, 1H), 8.00–7.50 (m, 5H), 3.89 (s, 3H), 3.70 (s, 3H), 3.17–3.11 (m, 1H), 1.90–1.88 (m, 6H), 1.62–1.60 (m, 2H).

2-Propyl-3-propyl-5-fluoro-1H-indole

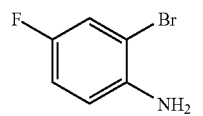

C$_6$H$_5$BrFN
Exact Mass: 188.96
Mol. Wt.: 190.01

Pr≡Pr

C$_8$H$_{14}$
Exact Mass: 110.11
Mol. Wt.: 110.2

$\xrightarrow{\text{Pd(OAc)}_2, \text{dtbpf}}_{\text{K}_2\text{CO}_3, \text{NMP}, 130°\text{C.}}$

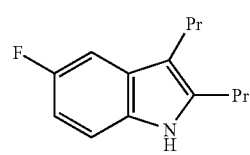

C$_{14}$H$_{18}$FN
Exact Mass: 219.14
Mol. Wt.: 219.3

A 50 mL three neck flask was charged with palladium acetate (22.4 mg, 0.1 mmol), dtbpf (94 mg, 0.2 mmol), potassium carbonate (690 mg, 5 mmol), 2-bromo-4-fluoroaniline (380 mg, 2 mmol), 4-octyne (264 mg, 2.4 mmol) and NMP (10 ml). The mixture was purged with argon and heated to 130° C. After 1 hr, the reaction mixture was cooled to rt. Ethyl acetate and water were added. The organic layer was separated and the aqueous layer was extracted with ethyl acetate. The combined organic phases were washed with water, brine and dried with MgSO$_4$. Removal of the solvents and purification of the crude by column chromatography afforded the desired product as yellow oil (355 mg, containing 4.3 wt % AcOEt). The corrected yield was 77.6%.

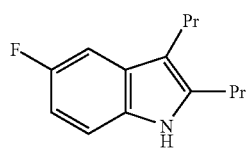

$^1$H NMR (400 MHz): δ=7.68 (s, 1H), 7.16–7.13 (m, 2H), 6.83 (td, 1H, J=9.2 Hz, J=2.4), 2.68 (t, 2H, J=7.6 Hz), 2.61 (t, 2H, J=7.6), 1.72–1.57 (m, 4H), 0.98 (t, 3H, J=7.2 Hz), 0.95 (t, 3H, J=7.2 Hz).

N-acetyl-2-Propyl-3-propyl-5-fluoro-indole and 2-Propyl-3-propyl-5-fluoro-1H-indole

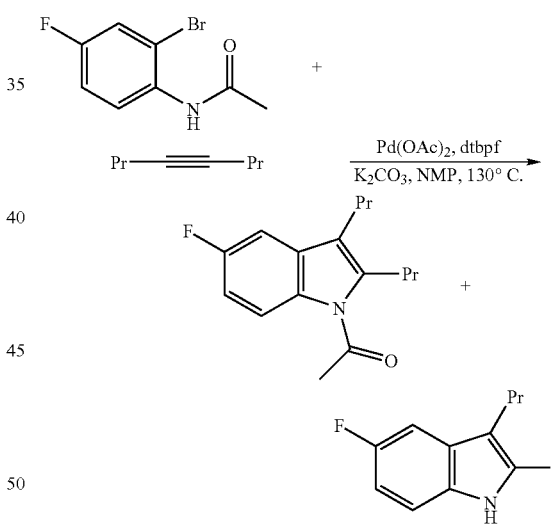

A 50 mL three neck flask was charged with palladium acetate (22.4 mg, 0.1 mmol), dtbpf (94 mg, 0.2 mmol), potassium carbonate (690 mg, 5 mmol), 2-bromo-4-fluoroacetanilide (464 mg, 2 mmol), 4-octyne (264 mg, 2.4 mmol) and NMP (10 mL). The mixture was purged with argon and heated to 130° C. After 1 hr, the reaction mixture was cooled to rt. Ethyl acetate and water were added. The organic layer was separated and the aqueous layer was extracted with ethyl acetate. The combined organic phases were washed with water, brine and dried with MgSO$_4$. Removal of the solvents and purification of the crude by column chromatography afforded a yellow oil as a mixture of the desired product and the corresponding deacelyated indole, in the ratio of 46:54 (407 mg, containing 7.7 wt % AcOEt). The corrected yield was 66%.

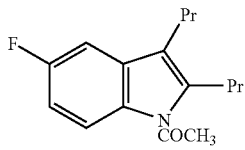

$^1$H NMR (400 MHz): δ=7.73 (m, 1H), 7.14 (m, 1H), 6.94 (td, 1H, J=9.2 Hz, J=2.4), 2.94 (t, 2H, J=7.6 Hz), 2.7 (s, 3H), 2.56 (t, 2H, J=7.6), 1.71 (m, 4H), 1.00–0.92 (m, 6H).

The invention claimed is:

1. A method for making substituted indole compounds comprising the steps of:

reacting a 2-bromoaniline or 2-chloroaniline of formula (I)

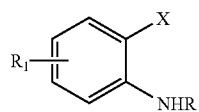

wherein:

X is Br or Cl,

R is H, alkyl, aryl, —C(O)C$_{1-6}$alkyl, —C(O)-aryl, —S(O)$_2$C$_{1-6}$alkyl or —S(O)$_2$aryl;

R$_1$ is C$_{1-6}$ alkyl, C$_{1-6}$ alkoxy, —CO$_2$ C$_{1-6}$ alkyl, C$_{1-6}$alkylHNC(O)—,

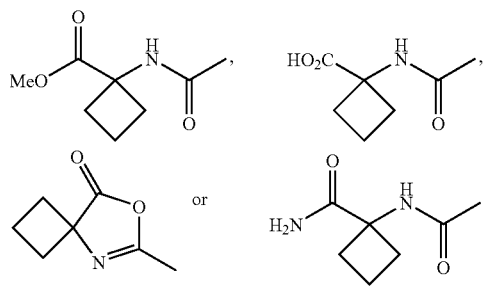

and with a substituted acetylene of formula (II)

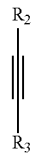

wherein

R$_2$ is acyclic or cyclic alkyl, aryl, or heterocycly;

R$_3$ is: phenyl optionally substituted with F, Cl, alkyl, aryl, CO$_2$C$_{1-6}$ alkyl or carboxamide, or R$_3$ is heteroaryl selected from pyridine, pyrimidine, furan, thiophene, pyrrole and imidazole, optionally substituted with F, Cl, alkyl, aryl, CO$_2$C$_{1-6}$ alkyl or carboxamide, or R$_3$ is trialkysilyl, alkyl, alkoxy;

in the presence of a palladium catalyst, a ligand, and a base in a solvent to give a compound of formula (III);

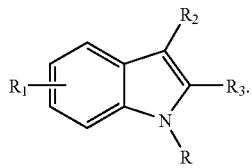

2. The process of claim 1 wherein the ligand used is selected from among:
   a) 1,1'-bis(di-alkylphosphino)ferrocene,
   b) trialkyphosphine, biphenyl dialkyphosphine,
   c) 1,1'-bis(di-t-butylphosphino)ferrocene,
   d) 1,1'-bis(di-iso-propylphosphino)ferrocene or tricyclohexylphosphine,
   e) 2-(di-t-butylphosphino)-biphenyl,
   f) 2-(di-t-butylphosphino)-2'-N,N-dimethylamino)biphenyl.

3. The process of claim 1 wherein the ligand used is selected from 1,1'-bis(di-t-butylphosphino)ferrocene, 1,1'-bis(di-iso-propylphosphino)ferrocene or tricyclohexylphosphine.

4. The process of claim 1 wherein the catalyst is selected from among Pd(OAc)$_2$, PdCl$_2$, PdBr$_2$, Pd$_2$(dba)$_3$, [Pd(ally)Cl]$_2$, Pd(CH$_3$CN)$_2$Cl$_2$, Pd(PhCN)$_2$Cl$_2$, Pd/C, encapsulated Pd and Pd(Cy$_3$P)$_2$Cl$_2$.

5. The process of claim 1 wherein the base is selected from the list consisting of K$_2$CO$_3$, KHCO$_3$, Na$_2$CO$_3$, CsOAc, KOAc, K$_3$PO$_4$, Cs$_2$CO$_3$, 1,8-diazabicyclo[5.4.0]undec-7-ene (DBU), tetramethyl guanidine (TMG), Bu$_4$N$^+$ OAc$^-$.

6. The process of claim 5 wherein the base is K$_2$CO$_3$.

7. The process of claim 1 wherein the solvent is selected from 1-methyl-2-pyrrolidinone (NMP), N,N-dimethylformamide (DMF), N,N-dimethylacetamide (DMAc), 4,4-dimethyl-2-imidazoline (DMI), or xylenes.

8. The process of claim 1 wherein the solvent is NMP or DMF.

9. The process of claim 1 wherein the palladium catalyzed indolization reaction is run at a temperature between 110° C. and 140° C.

10. The process of claim 1 wherein the solvent is NMP, the base is K$_2$CO$_3$, the catalyst is Pd(OAc)$_2$, and the ligand is 1,1'-bis(di-t-butylphosphino)ferrocene.

* * * * *